United States Patent
Allen, IV

(10) Patent No.: US 11,660,158 B2
(45) Date of Patent: *May 30, 2023

(54) ENHANCED HAPTIC FEEDBACK SYSTEM

(71) Applicant: Covidien LP, Mansfield, MA (US)

(72) Inventor: James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/465,956

(22) Filed: Sep. 3, 2021

(65) Prior Publication Data

US 2021/0393358 A1 Dec. 23, 2021

Related U.S. Application Data

(63) Continuation of application No. 16/385,133, filed on Apr. 16, 2019, now Pat. No. 11,109,930.

(Continued)

(51) Int. Cl.
*A61B 34/00* (2016.01)
*G06F 3/01* (2006.01)
*A61B 17/32* (2006.01)

(52) U.S. Cl.
CPC .............. *A61B 34/76* (2016.02); *A61B 17/32* (2013.01); *A61B 34/25* (2016.02); *G06F 3/016* (2013.01)

(58) Field of Classification Search
CPC ......... A61B 34/76; A61B 34/25; G06F 3/016; G06F 3/0304; G06F 3/0308
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Michael Choti, "Abdominoperineal Resection with the LigaSure Vessel Sealing System and LigaSure Atlas 20 cm Open Instrument" Innovations That Work, Jun. 2003.
(Continued)

*Primary Examiner* — Benyam Haile
(74) *Attorney, Agent, or Firm* — Carter, DeLuca & Farrell LLP

(57) ABSTRACT

An enhanced haptic feedback system for medical diagnostics includes a laparoscope configured to be inserted into a body cavity to view tissue and obtain an image of the viewed tissue. An imaging device is configured to acquire physiological data about tissue, process the acquired physiological data, and output the processed data to a graphical user haptic interface (GUHI) capable of generating tangible sensations utilizing one or more haptic interfaces. The GUHI is configured to combine the image received from the laparoscope and the processed physiological data received from the imaging device to provide tangible sensations on both a front screen of the GUHI and a rear screen of the GUHI allowing a surgeon the sensation of feeling for abnormal tissue conditions between the surgeon's hands.

20 Claims, 2 Drawing Sheets

Related U.S. Application Data

(60) Provisional application No. 62/682,204, filed on Jun. 8, 2018.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 11,109,930 B2 | 9/2021 | Allen, IV |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2017/0042626 A1* | 2/2017 | Egorov ............ A61B 1/00194 |
| 2017/0071688 A1* | 3/2017 | Cohen ................ A61B 17/29 |
| 2018/0168740 A1* | 6/2018 | Ryan .................. A61B 90/36 |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3627221 A1 | 2/1988 |
| DE | 8712328 | 3/1988 |
| DE | 04303882 C2 | 2/1995 |
| DE | 3430858202 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 1004537502 | 10/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1159926 A2 | 12/2001 |
| EP | 1281878 A1 | 2/2003 |
| JP | 61501068 | 9/1984 |
| JP | 55106 | 1/1993 |
| JP | H0540112 A | 2/1993 |
| JP | H06343644 A | 12/1994 |
| JP | H07265328 A | 10/1995 |
| JP | 08056955 | 3/1996 |
| JP | 08252263 | 10/1996 |
| JP | 8289895 | 11/1996 |
| JP | 8317934 | 12/1996 |
| JP | 8317936 | 12/1996 |
| JP | 09000538 | 1/1997 |
| JP | H0910223 A | 1/1997 |
| JP | 9122138 | 5/1997 |
| JP | 1024051 | 1/1998 |
| JP | 0010000195 | 1/1998 |
| JP | 10155798 | 6/1998 |
| JP | 1147149 | 2/1999 |

(56) References Cited

FOREIGN PATENT DOCUMENTS

| | | |
|---|---|---|
| JP | 1147150 | 2/1999 |
| JP | 11070124 | 3/1999 |
| JP | 11169381 | 6/1999 |
| JP | 11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2001003400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| JP | 6121797 B2 | 4/2017 |
| JP | 6285078 B2 | 2/2018 |
| JP | 6502328 B2 | 4/2019 |
| JP | 6511401 B2 | 5/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A3 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas MedicalCenter,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000, 6 pages.
Johnson et al. "Evaluation of a Bipolar Electrothermal Vessel Sealing Device in Hemorrhoidectomy" Sales/Product Literature; Jan. 2004, 1 page.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001, 1 page.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase 1 Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003. (15 pages.).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.

(56) References Cited

OTHER PUBLICATIONS

Crawford et al. "Use of the LigaSure Vessel Sealing System in Urologic Cancer Surger"; Grand Rounds in Urology 1999 vol. 1 Issue 4 pp. 10-17.

Craig Johnson, "Use of the LigaSure Vessel Sealing System in Bloodless Hemorrhoidectomy"; Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.. (1 page).

E. David Crawford, "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy"; Sales/Product Literature 2000.

Crouch et al. "A Velocity-Dependent Model for Needle Insertion in Soft Tissue"; MICCAI 2005; LNCS 3750 pp. 624-632, Dated: 2005.

McLellan et al., "Vessel Sealing for Hemostasis During Pelvic Surgery" Int'l Federation of Gynecology and Obstetrics Figo World Congress 2000, Washington, DC.

McLellan et al. "Vessel Sealing for Hemostasis During Gynecologic Surgery" Sales/Product Literature 1999.

U.S. Appl. No. 08/926,869, filed Sep. 10, 1997; inventor: James G. Chandler (abandoned).

U.S. Appl. No. 09/177,950, filed Oct. 23, 1998; inventor: Randel A. Frazier (abandoned).

U.S. Appl. No. 09/387,883, filed Sep. 1, 1999; inventor: Dale F. Schmaltz (abandoned).

U.S. Appl. No. 09/591,328, filed Jun. 9, 2000; inventor: Thomas P. Ryan (abandoned).

U.S. Appl. No. 12/336,970, filed Dec. 17, 2008; inventor: Paul R. Sremeich (abandoned).

U.S. Appl. No. 14/065,644, filed Oct. 29, 2013; inventor: Reschke (abandoned).

Heniford et al. "Initial Research and Clinical Results with an Electrothermal Bipolar Vessel Sealer" Oct. 1999.

\* cited by examiner

ENHANCED HAPTIC FEEDBACK SYSTEM

CROSS REFERENCE TO RELATED APPLICATION

The present application is a continuation application of United States application Ser. No.: 16/385,133 filed on Apr. 16, 2019, which claims the benefit of and priority to U.S. Provisional Application Ser. No. 62/682,204, filed on Jun. 8, 2018 the entire contents of each of which are incorporated herein by reference.

BACKGROUND

Technical Field

The present disclosure relates to monitoring instruments for minimally invasive surgical procedures and, more particularly, to an enhanced haptic feedback system for use with various laparoscopic surgical procedures.

Description of Related Art

In minimally invasive surgery (MIS) and various percutaneous procedures, limited visibility and limited anatomical feedback can often supersede the advantages of the procedure and put the surgeon at a relative disadvantage compared to open procedures. Moreover, many MIS procedures require additional incisions to accommodate an endoscope to improve visibility. These additional instruments typically do not provide any tactile feedback which may be advantageous during particular types of procedures, e.g., tactile feedback allows a surgeon to appreciate relevant physiological information about biological tissues and allows an interactive experience through a haptic interface while operating.

Rudimentary haptic interfaces have been used in gaming, e.g., gaming controllers, however, in the medical field, haptic technology has mostly been limited to simulators for various medical procedures in a virtual environment, for example, for teaching purposes.

Medical companies have also implemented haptic feedback systems that provide notification signals and/or vibrotactile sensations as an alert when too much force is applied or to direct user controlled systems or robotic/tele-surgical operating systems. However, these systems do not provide the operator with tangible sensations that are physiologically relevant or reliable, nor do they provide a corresponding visual user interface that conveys the tactile information along with visual images of the body tissue.

SUMMARY

As used herein, the term "distal" refers to the portion that is being described which is further from a user, while the term "proximal" refers to the portion that is being described which is closer to a user.

In accordance with one aspect of the present disclosure, an enhanced haptic feedback system for medical diagnostics includes a laparoscope configured to be inserted into a body cavity of a patient to view internal tissue and tissue structures, the laparoscope is electrically coupled to a graphical user interface (GUI) configured to display an image of the tissue thereon or obtain an image of the tissue. An imaging device is included and is configured to acquire physiological data about tissue, process the acquired physiological data, and output the processed data to a graphical user haptic interface (GUHI) capable of generating tangible sensations utilizing one or more haptic interfaces. The GUHI is configured to combine the image received from the laparoscope and the processed physiological data received from the imaging device to provide tangible sensations on both a front screen of the GUHI and a rear screen of the GUHI allowing a surgeon the sensation of feeling for abnormal tissue conditions between the surgeon's hands. Normal tissue properties may be assessed in this fashion as well.

In aspects according to the present disclosure, the imaging device is selected from the group consisting of an ultrasound device, a magnetic resonance imaging (MRI) device, a computerized axial tomography (CT) scanner, and a functional magnetic resonance imaging (fMRI) device. In other aspects, the imaging device is a portable ultrasound probe. In still other aspects, the GUHI is portable and is configured to be held between the surgeon's fingers and thumb.

In yet other aspects, the imaging device is configured to acquire and process physiological data about tissue in real time and combine the processed physiological data about tissue with the image received from the laparoscope in real time. In still other aspects, the imaging device is configured to acquire and process physiological data about tissue prior to combining the processed physiological data with the image from the laparoscope.

In accordance with another aspect of the present disclosure, an enhanced haptic feedback system for medical diagnostics includes an imaging device configured to acquire physiological data about tissue, process the acquired physiological data, and output the processed data to a graphical user haptic interface (GUHI) capable of generating tangible sensations utilizing one or more haptic interfaces. The GUHI is configured to combine an image received from a laparoscope and the processed physiological data received from the imaging device to provide tangible sensations on both a front screen of the GUHI and a rear screen of the GUHI allowing a surgeon the sensation of feeling for abnormal tissue conditions between the surgeon's hands.

In aspects according to the present disclosure, the imaging device is selected from the group consisting of an ultrasound device, a magnetic resonance imaging (MRI) device, a computerized axial tomography (CT) scanner, and a functional magnetic resonance imaging (fMRI) device. In other aspects, the imaging device is a portable ultrasound probe. In still other aspects, the GUHI is portable and is configured to be held between the surgeon's fingers and thumb.

In yet other aspects, the imaging device is configured to acquire and process physiological data about tissue in real time and combine the processed physiological data about tissue with the image received from the laparoscope in real time. In still other aspects, the imaging device is configured to acquire and process physiological data about tissue prior to combining the processed physiological data with the image from the laparoscope.

The present disclosure also relates to a method for assessing tissue maladies ad includes positioning a laparoscopic or camera enabled device into a body cavity of a patient to visualize tissue and display a tissue image on a graphical user interface (GUI). The method also includes: acquiring physiological tissue data from an imaging source, combining both the acquired physiological data and the tissue image on a graphical user haptic interface (GUHI), and generating tangible sensations via one or more haptic interfaces on both a front screen of the GUHI and a rear screen of the GUHI allowing a surgeon to feel and diagnose various tissue maladies. Normal tissue properties may be assessed in this fashion as well.

BRIEF DESCRIPTION OF THE DRAWINGS

Various aspects of the present disclosure are described herein with reference to the drawings wherein like reference numerals identify similar or identical elements.

DETAILED DESCRIPTION

Throughout the description, any particular feature(s) of a particular exemplary embodiment may be equally applied to any other exemplary embodiment(s) of this specification as suitable. In other words, features between the various exemplary embodiments described herein are interchangeable as suitable, and not exclusive.

Various embodiments of the presently disclosed system enable surgeons to acquire, read, modify, store, write, and download acquired sensor data in real time and display the information on one or more haptic displays. A haptic display is a device that portrays a visual representation of an object (such as a computer monitor, television, or cell phone display) and combines surface haptics overlayed on the image, producing variable forces on a user's finger as it interacts with the surface haptics. This can give the illusion of feeling textures and three dimensional shapes as the user touches the image on the screen.

CT scans, MRIs, fMRIs and ultrasound probes can detect, among other things, density of tissue. This acquired sensor data can be combined with images of actual tissue in real time. For example, if a laparoscope is used to view the surgical site, the location and orientation of the camera can be tracked so that the focal point has a known location within the patient. Using this known location, density data from a previous scan, e.g., a CT scan or MRI, and even real-time data from a live ultrasound probe (portable or standalone) can be used to overlay haptic data on a screen that the surgeon can then feel with his or her own hands.

Figure 1:
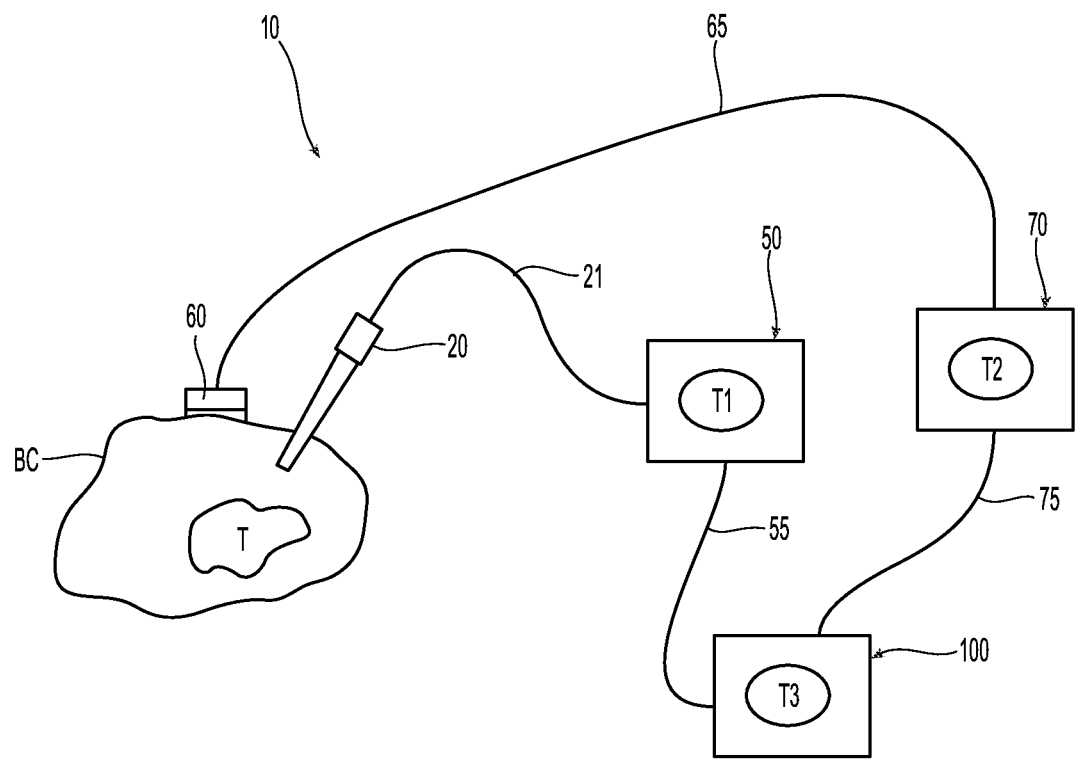
FIG. 1 is a schematic view of a surgical system including an enhanced haptic feedback system including a laparoscope, a display and a graphical user haptic interface (GUHI) according to the present disclosure.
Figure 2:
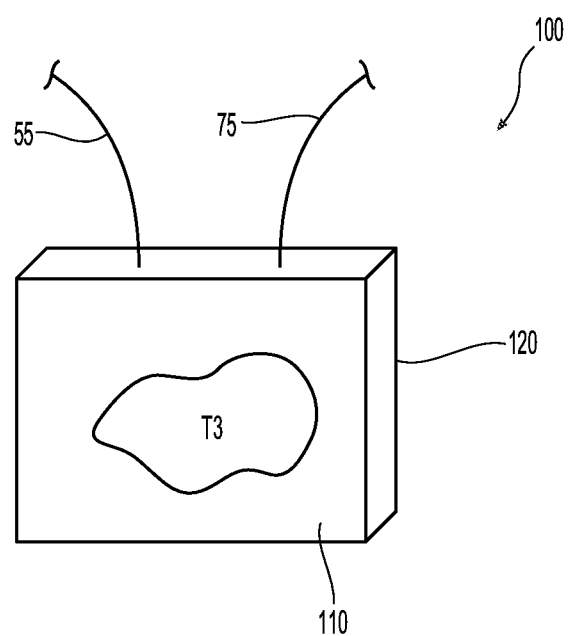
FIG. 2 is an enlarged view of the GUHI of FIG. 1.

Referring now to FIGS. 1 and 2, an enhanced haptic display system is shown and is generally identified as haptic system 10. Haptic system 10 includes a surgical camera 20 which may be an endoscope or laparoscope 20 operatively coupled via a cable 21 to a graphical user interface (GUI) 50 for displaying images "T1" of tissue "T" disposed within a body cavity "BC" of a patient. An imaging device 70 is included and includes a probe 60 electrically coupled via cable 65 to the imaging device 70. Imaging device 70 may be an ultrasound probe 60 that is configured to render images of tissue "T" in real time or imaging device 70 may be CT scan, MRI, FMRI or any other type of imaging device capable of acquiring sensor data relating to tissue or organs either in real time or prior to using the haptic system 10. Imaging device 70 is configured to measure various tissue properties, e.g., tissue density, blood flow, etc., and convert the acquired sensed data to haptic signal data readable and displayable by a graphical user haptic interface (GUHI) 100.

GUHI 100 is operatively coupled via cable 75 to the GUI 50 and is configured to display images of the tissue "T3" overlapped with acquired sensor data (haptic data) obtained from imaging device 70. In various embodiments, the haptic system 10 communicates with the operator (e.g., surgeon) using a symbolic language descriptive of biological tissues physical properties and the characteristics of motors and actuators that constitute the interactive components of one or more haptic interfaces. Typically the haptic system 10 includes a touch screen interface, e.g., front screen 110 or rear panel or rear screen 120 (FIG. 2), which can provide haptic signals to the user and is thus an active display with touch and/or feedback that programs the one or more haptic interfaces. The haptic system 10 may include haptic signals that confirm programmable or system features (e.g., a palpable click) and provide additional sensor feedback that is descriptive of the events occurring in the haptic interfaces (e.g., vibro-tactile feedback, haptic rendering of physiologic events, audible and visual cues).

In embodiments, modification of the haptic experience of a user may be accomplished in real time (e.g. during procedures). Visual icons 130a and secondary notations 130b (see FIG. 3) may be included to provide a simplified graphical format and to augment the haptic feedback to further reflect relevant physiological information. The various haptic interfaces provide a way to display acquired sensor data from one or more imaging sources 70, and control the corresponding actions of one or more corresponding actuators or haptic elements within the screen, e.g., screen 110 and/or screen 120.

The symbolic language communicated by the imaging device 70 provides the acquired sensor data in both frequency and time and enables a user-friendly means for understanding, interacting with and controlling hardware, firmware and programming software in real time. The presently disclosed haptic system 10 provides an open, universally compatible platform capable of sensing or acquiring physiological signals/data (referred to as acquired sensor data) in any format; processing of the acquired sensor data within an operating system; and outputting the processed signals to the GUHI 100 which generates tangible sensations via one or more haptic interfaces. Tangible sensations are able to be felt or modified by the surgeon in real time on the GUHI 100 which allows a surgeon to feel and diagnose various tissue types and tissue maladies, e.g., tumors. Normal tissue properties may be assessed in this fashion as well.

The GUHI 100 utilizes various haptic interfaces including motors, actuators, and haptic elements to provide tactile feedback to the surgeon concerning the tissue. For example, the imaging device 70 may provide acquired sensor data to the GUHI 100 concerning tissue density of a liver. During a liver resection, a surgeon may need to feel for lumps in the liver in order to identify the appropriate plane of dissection that will excise an appropriate margin of healthy tissue on the patient side. This is to ensure that all of the cancer is removed, and only healthy tissue is left within the patient. As such, using the haptic system 10, the surgeon can feel the varying densities of the liver and quickly ascertain lumps or abnormal tissue masses to define an acceptable dissection plane.

FIG. 2 shows an enlarged view of the GUHI 100 and includes a front screen 110 and a rear panel or rear screen 120. The acquired sensor data from the imaging device 70 (and image "T2" if available) along with the image of the tissue "T1" from the laparoscope 20 are combined and displayed on the front screen 110 as tissue image "T3". More particularly, the image "T1" from the laparoscope is displayed on the front screen 110 and the surface haptics from the acquired sensor data is overlaid on the image "T2" to produce an image "T3" that provides variable forces on a user's fingers or hand as the user interacts with the surface of the front screen 110. As a result, the user is given the illusion of feeling textures as the user touches the image "T3" on the front screen 110.

The acquired haptic data can also be combined with images of the actual tissue in real time. For example, the location and orientation of the laparoscope can be tracked so that the focal point has a known location within the patient. Using this known location, density data from a previous CT scan or MRI or even real time data from a live ultrasound probe may be used to overlay surface haptics from the acquired sensor data on the front screen 110.

Figure 3:
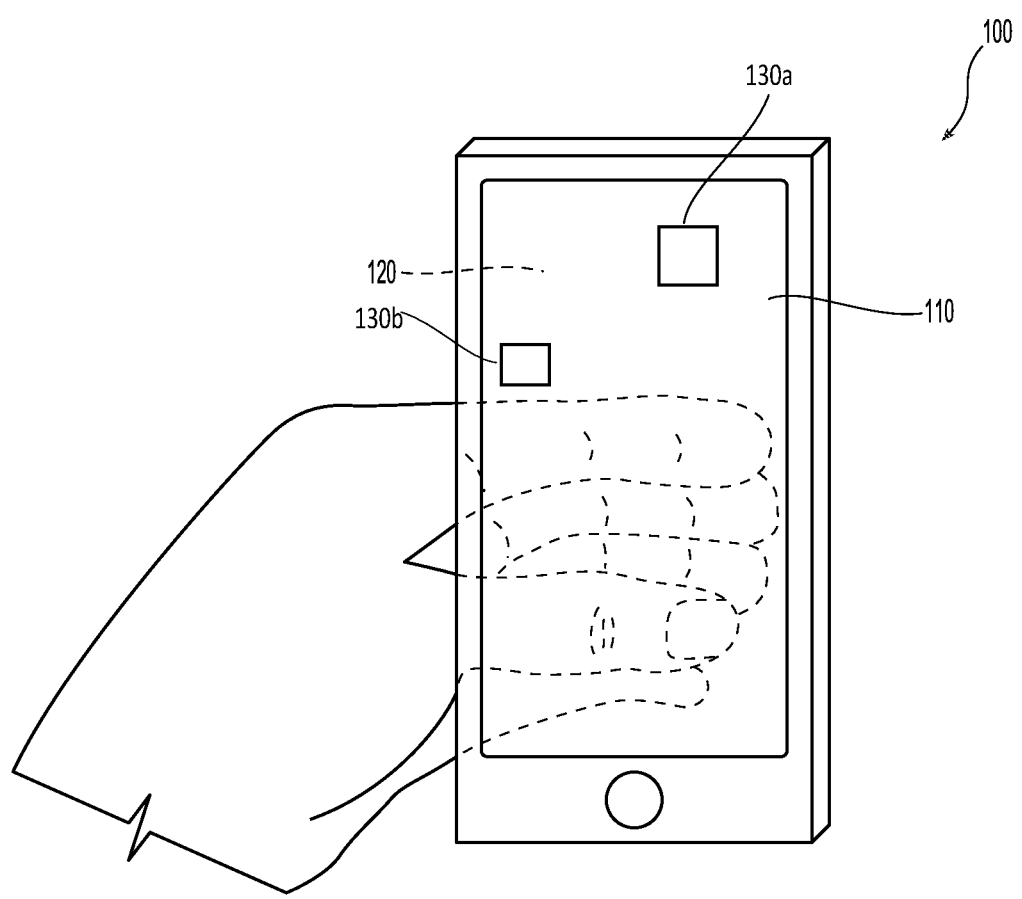
FIG. 3 is an enlarged, schematic view of the GUHI of FIG. 1 shown in use.

The surface haptics from the acquired sensor data may also be overlaid on the rear screen 120. This would give the surgeon the ability to feel three dimensional objects such as a lump more effectively. For example, the surgeon can put his or her hand around the GUHI 100 (around both the front and rear screens 110, 120, respectively) and feel objects between his/her thumb and fingers (FIG. 3). It is contemplated that utilizing both the front screen 110 and the rear screen 120 as haptic surfaces will enhance medical diagnostics, e.g., for more effectively analyzing mammograms.

The disclosure also relates to a method for operating a haptic system 10 including positioning a laparoscopic or camera-enabled device 20 into a body cavity "BC" to visualize tissue "T" and displaying a tissue image "T1" on a GUI 50. The method also includes obtaining imaging information "T2" or physiological tissue data (acquired sensor data) from an imaging source (CT scan, MRI, fMRI, ultrasound, etc.), displaying a tissue image "T3" on a GUHI 100, overlaying the acquired sensor data on the tissue image "T3", and generating tangible sensations via one or more haptic interfaces on both the front screen 110 of the GUHI 100 and the rear screen 120 of the GUHI 100 relating to one or more tissue properties, e.g., tissue density. Tangible sensations may be felt by the surgeon in real time on the GUHI 100 which allows a surgeon to feel and diagnose various tissue types and tissue maladies, e.g., tumors.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A haptic feedback system for medical diagnostics, comprising:
 a surgical camera configured to obtain an image of tissue in a body;
 an imaging device configured to acquire physiological data about the tissue, convert the acquired physiological data into haptic signal data, and output the haptic signal data; and
 a graphical user haptic interface (GUHI), the GUHI configured to receive and combine the image from the surgical camera and the haptic signal data from the imaging device and generate tangible sensations on at least one of a front screen or a rear screen utilizing at least one haptic interface based on the combined image and haptic signal data.

2. The haptic feedback system for medical diagnostics according to claim 1, wherein the imaging device is at least one of an ultrasound device, a magnetic resonance imaging (MRI) device, a computerized axial tomography (CT) scanner, portable ultrasound probe, or a functional magnetic resonance imaging (fMRI) device.

3. The haptic feedback system for medical diagnostics according to claim 1, wherein the GUHI is portable and is configured to be held between a user's fingers and thumb.

4. The haptic feedback system for medical diagnostics according to claim 1, wherein the imaging device is configured to acquire physiological data about tissue and convert the physiological data into haptic signal data in real time.

5. The haptic feedback system for medical diagnostics according to claim 4, wherein the GUHI is further configured to combine the haptic signal data with the image from the surgical camera in real time.

6. The haptic feedback system for medical diagnostics according to claim 1, wherein the imaging device is configured to acquire and convert the physiological data into haptic signal data prior to the GUHI combining the haptic signal data with the image from the surgical camera.

7. The haptic feedback system for medical diagnostics of claim 1, further comprising a graphical user interface (GUI) operatively coupled to the GUHI, the GUI configured to display the image from the surgical camera.

8. The haptic feedback system for medical diagnostics of claim 1, wherein the GUHI is further configured to display at least one of visual icons or secondary notations on at least one of the front or rear screens.

9. The haptic feedback system for medical diagnostics of claim 1, wherein the tangible sensations include at least one of a click, vibro-tactile feedback, haptic rendering of physiologic events, audible cues, or visual cues.

10. A robotic surgical system comprising:
a surgical robotic arm configured to enable remote operation of a surgical instrument;
a surgical camera coupled to the surgical robotic arm and configured to be inserted into a body cavity to view and obtain an image of tissue;
an imaging device configured to acquire physiological data about the tissue, convert the acquired physiological data into haptic signal data, and output the haptic signal data; and
a graphical user haptic interface (GUHI), the GUHI configured to receive and combine the image from the surgical camera and the haptic signal data from the imaging device and generate tangible sensations on at least one of a front screen or a rear screen utilizing at least one haptic interface based on the combined image and haptic signal data.

11. The robotic surgical system of claim 10, further comprising a work station configured to enable a medical professional to control at least one of the surgical robotic arm or the GUHI.

12. The haptic feedback system for medical diagnostics according to claim 11, wherein the GUHI is portable and is configured to be held between the medical professional's fingers and thumb.

13. The haptic feedback system for medical diagnostics according to claim 10, wherein the imaging device is at least one of an ultrasound device, a magnetic resonance imaging (MRI) device, a computerized axial tomography (CT) scanner, portable ultrasound probe, or a functional magnetic resonance imaging (fMRI) device.

14. The haptic feedback system for medical diagnostics according to claim 10, wherein the imaging device is configured to acquire physiological data about tissue and convert the physiological data into haptic signal data in real time.

15. The haptic feedback system for medical diagnostics according to claim 10, wherein the GUHI is further configured to combine the haptic signal data with the image from the surgical camera in real time.

16. The haptic feedback system for medical diagnostics according to claim 10, wherein the imaging device is configured to acquire and convert the physiological data into haptic signal data prior to the GUHI combining the haptic signal data with the image from the surgical camera.

17. The haptic feedback system for medical diagnostics of claim 10, further comprising a graphical user interface (GUI) operatively coupled to the GUHI, the GUI configured to display the image from the surgical camera.

18. A method for assessing tissue maladies, comprising:
inserting a surgical camera into a body cavity to visualize tissue and obtain a tissue image;
acquiring physiological tissue data from an imaging source;
combining the acquired physiological data and the tissue image for display on a graphical user haptic interface (GUHI);
displaying the tissue image on at least one of a front screen and a rear screen of the GUHI; and
generating tangible sensations via one or more haptic interfaces on at least one of the front or rear screens of the GUHI.

19. The method for assessing tissue maladies of claim 18, wherein combining the physiological data and the tissue image further comprises converting the physiological data into haptic signal data.

20. The method for assessing tissue maladies of claim 18, further comprising:
tracking the location and orientation of the surgical camera to determine a known location of a focal point of the surgical camera; and
based on the known location, displaying density data as an overlay on at least one of the front or rear screen.

* * * * *